United States Patent [19]

Obrez

[11] 4,169,464
[45] Oct. 2, 1979

[54] CATHETER FOR SELECTIVE CATHETERIZATION OF AORTIC BRANCHES

[75] Inventor: Ivo Obrez, Brookline, Mass.
[73] Assignee: Cordis Corporation, Miami, Fla.
[21] Appl. No.: 861,456
[22] Filed: Dec. 16, 1977
[51] Int. Cl.² ............................................. A61M 25/00
[52] U.S. Cl. ................................... 128/657; 128/348; 128/DIG. 9; 128/658
[58] Field of Search ......... 128/2.05 R, 2 M, 348–350, 128/214.4, 239, DIG. 9, DIG. 26

[56] References Cited

U.S. PATENT DOCUMENTS

| | | | |
|---|---|---|---|
| 3,773,034 | 11/1973 | Burns et al. | 128/2 M |
| 3,924,633 | 12/1975 | Cook et al. | 128/349 R |
| 3,938,501 | 2/1976 | Erikson | 128/2 A |
| 4,033,331 | 7/1977 | Guss et al. | 128/348 X |
| 4,072,146 | 2/1978 | Howes | 128/348 X |
| 4,117,836 | 10/1978 | Erikson | 128/348 X |

OTHER PUBLICATIONS

"USCI-Positrol II Judkins Type Transfemoral Coronary and Ventriculography Catheters" Catalogue, 12-73/5070082

*Primary Examiner*—E. H. Eickholt
*Attorney, Agent, or Firm*—Kenway & Jenney

[57] ABSTRACT

A multipurpose catheter and techniques for selective catheterization of branches arising from the aorta. The catheter tip is an incomplete turn of a coil formed in three dimensions and terminating in an extremity which is tangent to, or reversed slightly in direction to, the direction of the winding of the coil. The diameter of the coil is chosen substantially to match that of the aortic lumen at the level of the branch to be catheterized for improved stability, especially during the injection of contrast media. Side holes may be formed in the side of the loop in addition to that at the extremity of the tip in order that semi-selective angiograms may be obtained. In addition to matching the diameter of the coil to that of the aortic lumen at a specific level, the catheterization involves gentle rotation of the catheter, a technique which can be mastered without extensive experience in angiography.

4 Claims, 5 Drawing Figures

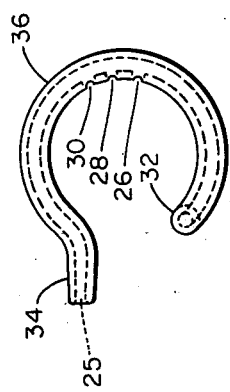
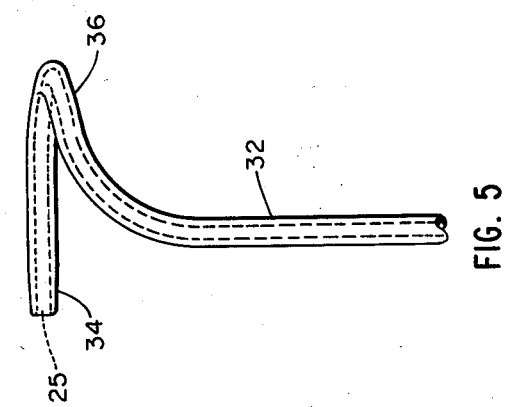
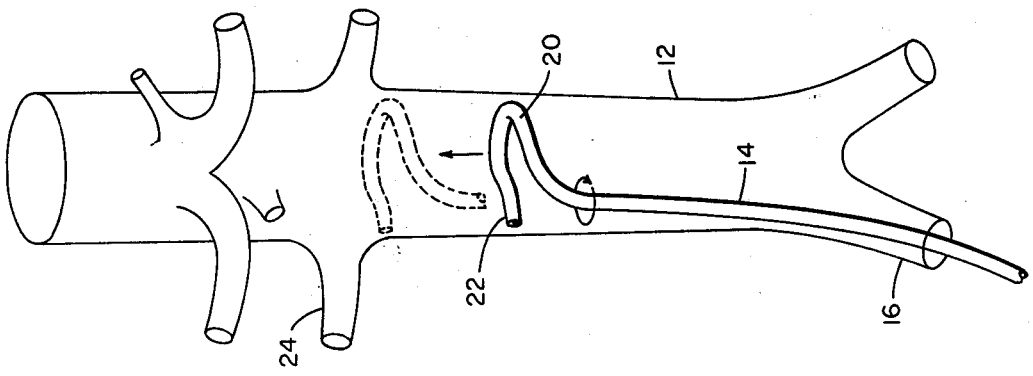
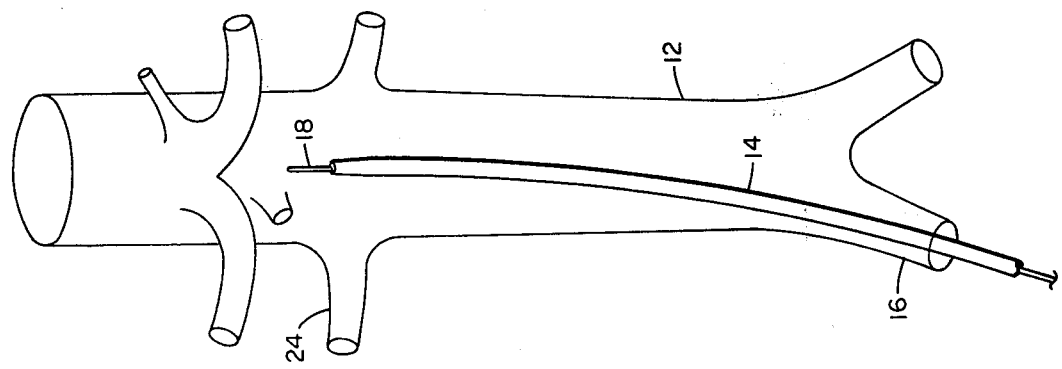

CATHETER FOR SELECTIVE CATHETERIZATION OF AORTIC BRANCHES

BACKGROUND OF THE INVENTION

Selective catheterization of aortic branches has been practiced for a number of years and many different catheter tips have been designed. With very few exceptions, however, even though these tips may be curved in various lengths and directions, they are two-dimensional. As a result, selective catheterization of an aortic branch, no matter what the configuration of the tip may be, becomes largely a matter of operator skill and experience.

With such catheters, occasionally with the aid of steering instruments, highly trained operators can usually obtain selective angiograms of adequate quality. In technically difficult cases, however, (e.g. in patients with marked tortuosity, displacement or dilation of the abdominal aorta), an angiographer may fail to catheterize selectively a specific branch of the aorta.

Another problem arises during the selective injection of contrast media into some aortic branches. The injection may be made manually or by power, but with power injection particularly, recoil of the two-dimensional catheters now in use may preclude an adequate filling of the vessel.

The principal object of this invention is to permit less experienced angiographers successfully to perform selective catheterization of aortic branches, despite the condition of the aorta. Another object is generally to facilitate selective catheterization of aortic branches and to stabilize the catheter tip during the injection of contrast media and thus ensure proper filling of the vessel being catheterized.

BRIEF DESCRIPTION OF THE INVENTION

The present invention involves a three-dimensional catheter tip which is formed as an incomplete turn of a three-dimensional coil or which may be terminated in an extremity which is tangent to, or turned back slightly in a direction generally opposite that of, the winding of the coil turn. The direction of winding of the coil turn may be either clockwise or counterclockwise. The tip may have, in addition to an axial opening at its extremity, a side opening or openings through the inner wall of a portion of the coil.

The catheter is preferably formed of radio-opaque thermoplastic material such as polyethylene or polyurethane. Braided wire may be incorporated in the material forming the catheter wall for reinforcement purposes.

The diameter of the coil turn preferably is matched to that of the aortic lumen adjacent the origin of the branch to be catheterized. The catheter is inserted by the Seldinger method and advanced over a guide wire to the specific desired level under fluoroscopic observation. After withdrawal of the guide wire, the catheter tip resumes its shape and it may then be gently rotated in the direction opposite to that of the winding of the coil while it is advanced or withdrawn to reach the desired level of the aorta. Further gentle rotation of the coil in the direction of the winding of the coil then permits selective catheterization of a specific aortic branch. Injection of contrast media causes slight expansion of the coil against the surrounding lumen with accompanying increase in stability of the tip.

For a better understanding of the invention, its objects, features, and advantages, there follows a detailed description of a preferred embodiment and method of practicing the invention which should be read in connection with the appended drawing in which:

BRIEF DESCRIPTION OF THE DRAWING

FIG. 1 illustrates the catheter being advanced over its guide wire to a specific level of descending aorta, FIG. 2 shows the catheter resuming its shape after withdrawal of the guide wire, the arrows and portion in phantom indicating manipulation of the catheter, FIG. 3 shows the catheter in position for selective angiography, FIG. 4 is a top view of a preferred catheter in which side holes are formed to provide contrast media at the very origin of aortic branches, and FIG. 5 is a front view of a preferred catheter illustrating the three-dimensional nature of a preferred catheter.

DESCRIPTION OF PREFERRED EMBODIMENT

In FIG. 1, the descending aorta 12 is shown in part. The catheter 14 has been inserted through the femoral artery 16, part of which is shown in the drawing. The method of insertion is the well-known Seldinger method, and a vessel dilator may be used to facilitate the insertion.

With the aid of observations continuously made by fluoroscope, the catheter is advanced over a guide wire 18 to a specific level in the descending aorta following which the guide wire is withdrawn.

In FIG. 2, the catheter is illustrated as it appears after the withdrawal of the guide wire. The catheter tip resumes its original shape, which is that of a three-dimensional incomplete single turn of a coil 20 formed in a given direction and which may further include an extremity 22 tangent to, or bent backward from, the direction of winding of the turn. The vertical arrow and dotted showing of the tip indicate the manipulation of the catheter in order that the tip may reach the exact level of the aorta at which the branch to be catheterized originates. In the manipulation, the catheter actually may be advanced or withdrawn slightly while it is simultaneously gently rotated in a direction opposite to that of the winding of the coil, the rotative motion being indicated by the arrow turned back upon itself.

In the preferred design, the slight reversal of direction of the extremity of the tip relative to the direction of winding of the coil aids the entry of the extremity into the desired branch as illustrated in FIG. 3, wherein gentle rotation of the tip in the direction of winding of the coil as indicated by the arrow causes entry of the extremity of the tip into a branch 24 to be catheterized. By reason of its relatively close matching of the coil diameter to that of the aorta adjacent the level to be catheterized, a levering action occurs which facilitates proper entry of the extremity into the branch to be catheterized.

Generally, the practice is first to flush the catheter with saline solution after the guide wire is withdrawn. After the manipulation and entry of the extremity of the tip into the specific aortic branch, contrast media may be injected either manually or by power. The force of the injection of the contrast media, especially under power, tends to expand the catheter coil against the lumen stabilizing its position. Such stability is useful and desirable in most instances, but care must be taken to avoid complete occlusion of a branch.

The tip is most stable in the aorta when the coil is generally perpendicular to the straight length of the catheter. In such instances, the coil, although actually three-dimensional, is at only a slight angle to a plane perpendicular to the axis of the aorta. However, as indicated in the drawing, many of the branches are oblique to the aorta, and in those situations, it is possible to adjust the angle of the coil slightly relative to the axis of the aorta without significant loss of stability. Of course, before removal of the catheter from the vascular system, it is desirable to reinsert the guide wire to straighten the coil.

In some situations wherein the aorta exhibits marked tortuosity or has been displaced due to atherosclerosis, tumor, scoliosis, or other causes, the three-dimensional configuration has proven to be particularly valuable compared to catheters having two-dimensional tips. Such prior art devices are generally bent one or more times in a single plane which includes the straight portion of the catheter. Selective catheterization of branches arising from the convex portion of a dilated or tortuous aorta can be extremely difficult whereas the coil of the catheter of the present invention is relatively independent of the longitudinal curve of the aorta depending for its action mainly upon the inner wall of the aorta immediately adjacent the branch to be catheterized.

In FIG. 4, the catheter tip of the present invention is shown in the configuration in which it is originally formed and to which the memory of the material causes it to return when the guide wire is withdrawn. The catheter tip includes a single incomplete (or not entirely closed) turn 36 formed at a slight angle to a plane perpendicular to the straight length 32 of the catheter. The extremity of the tip is a short length 34 bent back outwardly or tangent to the coil periphery. It has been noted that coil diameters of 10 to 18 mm will serve most purposes in the descending aorta and with such diameters an extremity having a length of about 4 mm has proven satisfactory.

In the tip shown in FIG. 4, in addition to an opening 25 in the extremity of the tip, additional openings 26, 28 and 30 are formed in the inner wall of the coil. These openings make it possible to perform semi-selective renal angiograms as well as other investigations when it is desirable to see the origin of the vessel being catheterized. In some instances, a single side opening will suffice. Contrast media flows not only through the extremity of the catheter but also through the side opening or openings permitting semi-selective angiograms of good quality to be obtained.

As noted above, the catheter of the invention functions best when the coil diameter closely matches the diameter of the aortic lumen at the specific level of catheterization. Available data indicates that five standard sizes of coil diameter running from 10 to 18 mm are sufficient to perform selective catheterization in the majority of patients. Clinical experience reflects a high rate of success in the selective catheterization of aortic branches. As an example, the following table indicates the rate of success in catheterizing abdominal vessels:

TABLE I

TYPE AND NUMBER OF ANGIOGRAPHIC EXAMINATIONS RATE OF SUCCESS

| VESSEL | NUMBER OF EXAMINATION | SUCCESS Yes | No Introd Period | No Later | No Total |
|---|---|---|---|---|---|
| RENAL | 104 | 97 | 6 | 1 | 7 |
| CELIAC | 43 | 39 | 3 | 1* | 4 |
| SUP.MESENT. | 41 | 38 | 2 | 1* | 3 |
| INF.MESENT. | 12 | 10 | 2 | 0 | 2 |
| BRONCHIAL | 1 | 1 | — | — | — |
| INTERCOSTAL | 1 | 1 | — | — | — |
| PULM.SEQUESTR. | 1 | 1 | — | — | — |
| PHRENIC | 2 | 2 | — | — | — |
| LUMBAR | 5 | 4 | 1 | — | 1 |
| TOTAL | 210 | 193 | 14 | 3 | 17 |

*Patient with aneurysm of abdominal aorta

As noted above, the cited sizes of coil diameter are sufficient for use in the catheterization of abdominal branches. For other aortic branches, coils of other appropriate diameters may be formed.

Although the preferred embodiment shown and described has a unique configuration and the technique outlined involves specific steps, the advantages of the invention do not stem from only that embodiment or techniques but from the invention as claimed.

I claim:

1. A catheter for the selective catheterization of branches of the aorta comprising an elongated tubular member made of material having plastic memory and having a tip portion formed as an incomplete turn of a three-dimensional spiral coil terminating in an extremity extending outwardly from the direction of formation of said spiral coil.

2. A catheter as defined in claim 1 wherein said spiral coil has at least an opening formed in a side wall thereof.

3. A catheter as defined in claim 1 for catheterization of a specific aortic branch wherein the diameter of said spiral loop is preselected to substantially match that of the lumen of said aorta adjacent said specific aortic branch.

4. The method of selectively catheterizing branches of the aorta which comprises forming an incomplete turn of a three-dimensional spiral coil having an upwardly extending extremity at the end of a catheter made of radio-opaque tubing having plastic memory, inserting said catheter into said aorta over a guide wire to the vicinity of a selected aorta branch, withdrawing said guide wire to permit said tip to reform into said spiral coil and outwardly extending extremity, rotating said catheter to lodge said extremity in said selected branch and injecting contrast media through said catheter for discharge into said selected branch.

* * * * *